(12) United States Patent
Liu

(10) Patent No.: US 8,556,801 B2
(45) Date of Patent: Oct. 15, 2013

(54) COMBINED ENDOSCOPE AND SURGICAL INSTRUMENT GUIDE DEVICE

(76) Inventor: Jung-Tung Liu, Taichung (TW)

( * ) Notice: Subject to any disclaimer, the term of this patent is extended or adjusted under 35 U.S.C. 154(b) by 58 days.

(21) Appl. No.: 13/402,912

(22) Filed: Feb. 23, 2012

(65) Prior Publication Data

US 2013/0225921 A1    Aug. 29, 2013

(51) Int. Cl.
*A61B 1/00* (2006.01)
(52) U.S. Cl.
USPC .................. 600/114; 600/131; 600/102
(58) Field of Classification Search
USPC .......................................... 600/131
See application file for complete search history.

(56) References Cited

U.S. PATENT DOCUMENTS

| | | | | |
|---|---|---|---|---|
| 5,873,814 A * | 2/1999 | Adair | | 600/109 |
| 6,080,134 A * | 6/2000 | Lotti et al. | | 604/175 |
| 6,110,182 A * | 8/2000 | Mowlai-Ashtiani | | 606/130 |
| 6,221,007 B1 * | 4/2001 | Green | | 600/160 |
| 6,315,712 B1 * | 11/2001 | Rovegno | | 600/109 |
| 6,419,626 B1 * | 7/2002 | Yoon | | 600/109 |
| 6,554,765 B1 * | 4/2003 | Yarush et al. | | 600/132 |
| 6,782,288 B2 * | 8/2004 | Truwit et al. | | 600/429 |
| 7,214,183 B2 * | 5/2007 | Miyake | | 600/131 |
| D581,051 S * | 11/2008 | Melder | | D24/138 |
| 7,736,371 B2 * | 6/2010 | Schoepp | | 606/130 |
| 8,157,726 B2 * | 4/2012 | Melder | | 600/112 |
| 8,189,043 B2 * | 5/2012 | Schneider et al. | | 348/82 |
| 8,269,829 B2 * | 9/2012 | Miller et al. | | 348/82 |
| 2002/0022769 A1 * | 2/2002 | Smith et al. | | 600/188 |
| 2003/0055436 A1 * | 3/2003 | Daum et al. | | 606/130 |
| 2004/0054254 A1 * | 3/2004 | Miyake | | 600/104 |
| 2004/0133075 A1 * | 7/2004 | Motoki et al. | | 600/131 |
| 2004/0167543 A1 * | 8/2004 | Mazzocchi et al. | | 606/130 |
| 2004/0204628 A1 * | 10/2004 | Rovegno | | 600/131 |
| 2005/0085719 A1 * | 4/2005 | Franklin et al. | | 600/424 |
| 2005/0272975 A1 * | 12/2005 | McWeeney et al. | | 600/113 |
| 2006/0004258 A1 * | 1/2006 | Sun et al. | | 600/160 |
| 2006/0015014 A1 * | 1/2006 | Remijan et al. | | 600/182 |
| 2006/0167340 A1 * | 7/2006 | Pease et al. | | 600/127 |
| 2007/0185379 A1 * | 8/2007 | Newman et al. | | 600/110 |
| 2007/0249899 A1 * | 10/2007 | Seifert | | 600/109 |
| 2007/0276183 A1 * | 11/2007 | Melder | | 600/112 |
| 2008/0183191 A1 * | 7/2008 | Schoepp | | 606/130 |
| 2010/0033986 A1 * | 2/2010 | Schober et al. | | 362/555 |
| 2011/0295068 A1 * | 12/2011 | Petersen et al. | | 600/131 |
| 2011/0295271 A1 * | 12/2011 | Kao et al. | | 606/130 |

\* cited by examiner

*Primary Examiner* — John P Leubecker
*Assistant Examiner* — Arnaldo Torres Diaz

(57) ABSTRACT

An apparatus includes an endoscope and a surgical instrument guide device. An elongated surgical instrument is allowed to insert through a working channel of the endoscope to cooperate with a processor module of the endoscope. The surgical instrument guide device includes a base member, an adjustment member, a catch, a cap member, fasteners, and a tubing. Pegs of the catch are fitted in positioning holes of the base member. A tube of the endoscope is inserted through the tubing of the surgical instrument guide device so as to dispose in close proximity to a target.

3 Claims, 7 Drawing Sheets

COMBINED ENDOSCOPE AND SURGICAL INSTRUMENT GUIDE DEVICE

BACKGROUND OF THE INVENTION

1. Field of the Invention

The invention relates to endoscopes and more particularly to a combined endoscope and surgical instrument guide device.

2. Description of Related Art

Epidural or extradural hematoma is a type of traumatic brain injury (TBI) in which a buildup of blood occurs between the dura mater (the tough outer membrane of the central nervous system) and the skull. Often due to trauma, the condition is potentially deadly because the buildup of blood may increase pressure in the intracranial space and compress delicate brain tissue. Between 15 and 20% of epidural hematomas are fatal. For treating intracranial hematomas, a surgery may be performed to remove the blood mass and reduce the pressure it puts on the brain. The hematoma is evacuated through a burr hole or craniotomy.

There is a prior art endoscopic working channel for use in intracranial surgery. The endoscopic working channel comprises an inner solid tube and an outer tube. For removing intracranial hematomas, the endoscopic working channel is required to temporarily insert into the brain. Next, the inner tube is removed with the outer tube remained inside the skull during an endoscopy. However, the front end of the prior art endoscopic working channel is not capable of pivoting toward any one of north, east, south and west directions. Further, no medical instruments are allowed to insert into the endoscopic working channel.

There is a conventional surgical instrument guide device comprises a hollow base, a universal joint pivotably disposed in the base, an adjustment member through the universal joint, a catch provided within the base and contacted the universal joint, a cover having a hole, the cover being urged against the catch, and a support for stably holding the base on the skull. In a surgical operation, a medical employee may position a medical instrument using the surgical instrument guide device. Next, the medical employee may orient the medical instrument using an auxiliary device. Finally, the surgical instrument guide device is removed. As a result, the medical instrument is held in place.

A dentist may diagnose oral cavity of a patient using an intraoral camera in order to examine the conditions. The intraoral camera is a digital camera which is in data communication with a computer. Thus, a dentist may watch a monitor of the computer in order to find a solution to the patient's oral diseases. However, the front end of the conventional intraoral camera is not capable of pivoting toward any one of north, east, south and west directions. Further, the intraoral camera is not allowed to cooperate with any medical instruments.

Notwithstanding the prior art, the invention is neither taught nor rendered obvious thereby.

SUMMARY OF THE INVENTION

It is therefore one object of the invention to provide an endoscope comprising an elongated flexible tube; a housing integrally formed with a rear end of the tube and including a space; a working channel extending through both the tube and the housing; a tunnel extending from the space to a front end of the tube; a plurality of buttons disposed on the housing; a processor module disposed in both the space and the tunnel; and an electronic visual display disposed on top of the housing; wherein an elongated surgical instrument is allowed to insert through the working channel to cooperate with the processor module so that a clear image of a target can be taken by the processor module.

It is another object of the invention to provide an apparatus comprising an endoscope comprising an elongated flexible tube; a housing integrally formed with a rear end of the tube and including a space; a working channel extending through both the tube and the housing; a tunnel extending from the space to a front end of the tube; a plurality of buttons disposed on the housing; a processor module disposed in both the space and the tunnel; and an electronic visual display disposed on top of the housing; and a surgical instrument guide device for temporarily securing the endoscope to an organ of a patient; wherein an elongated surgical instrument is allowed to insert through the working channel to cooperate with the processor module so that a clear image of a target within the organ can be taken by the processor module.

The above and other objects, features and advantages of the invention will become apparent from the following detailed description taken with the accompanying drawings.

DETAILED DESCRIPTION OF THE INVENTION

Figure 1:
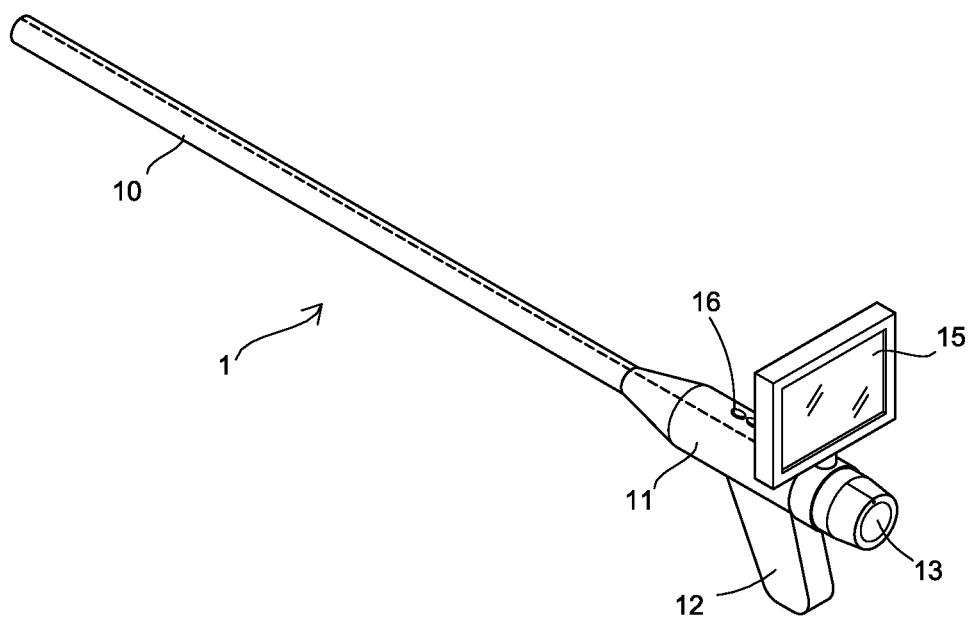
FIG. 1 is a perspective view of an endoscope according to the invention.
Figure 2:
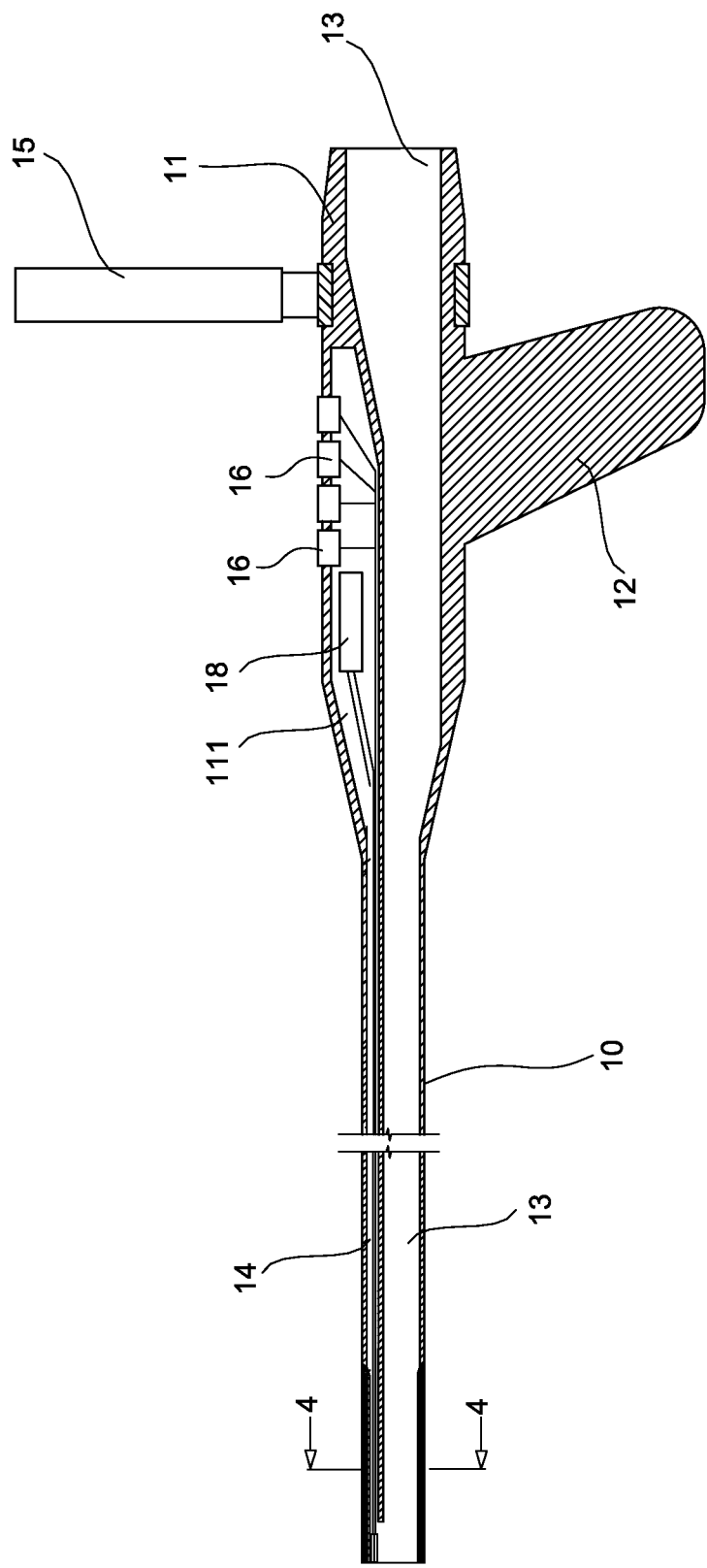
FIG. 2 is a longitudinal sectional view of the endoscope.
Figure 3:
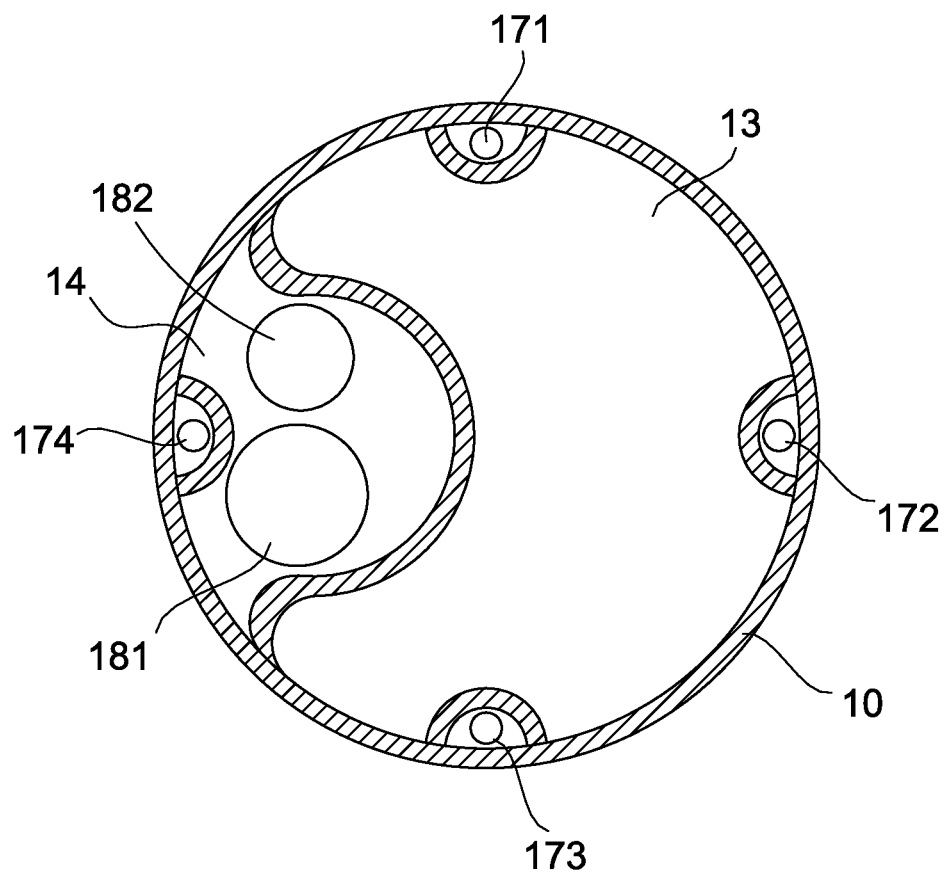
FIG. 3 is a sectional view taken along lines 4-4 of FIG. 2.
Figure 4:
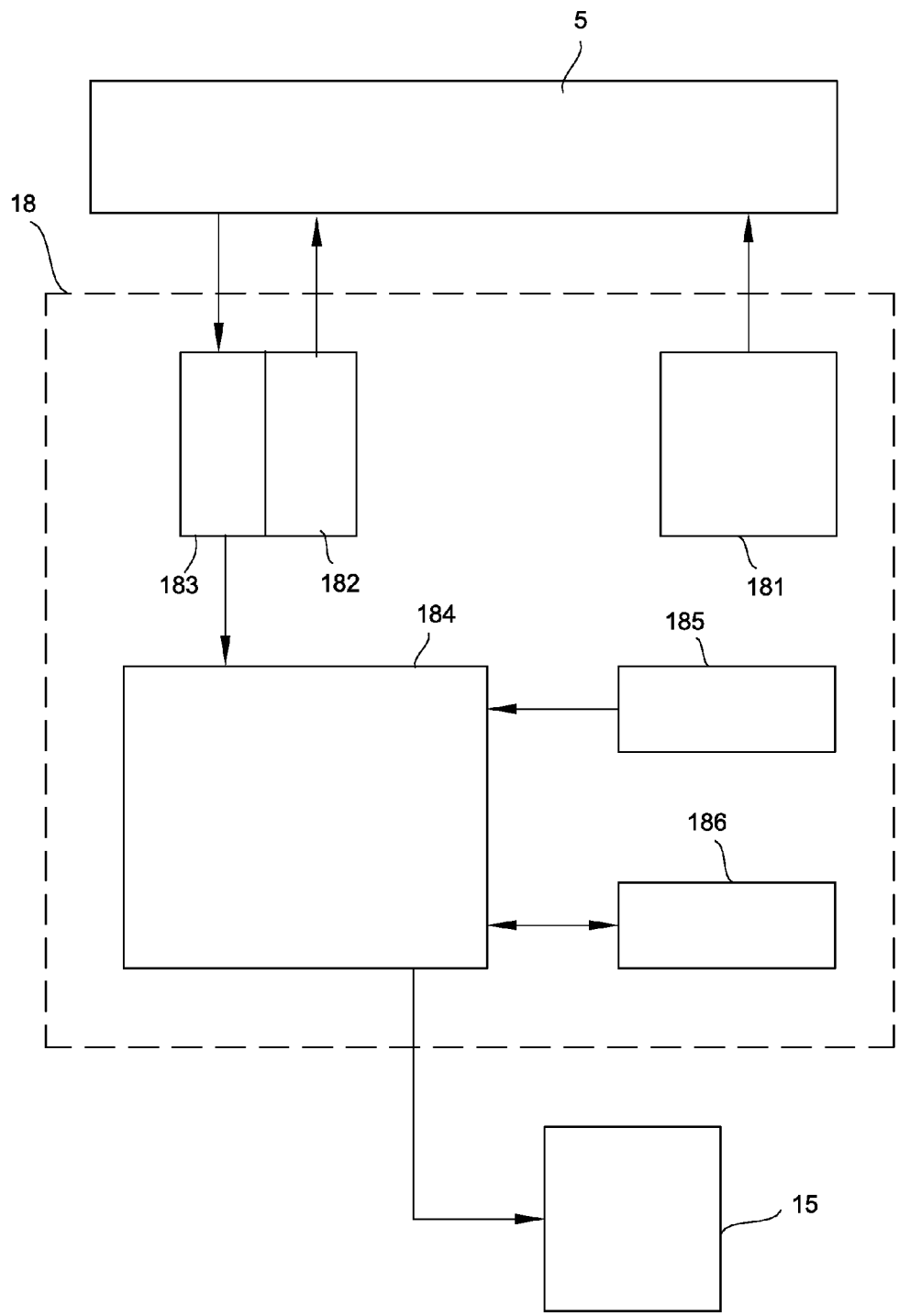
FIG. 4 is a block diagram of the processor module, the display, and an extradural hematoma.

Referring to FIGS. 1 to 7, a combined endoscope and surgical instrument guide device in accordance with the invention comprises the following components as discussed in detail below.

An endoscope 1 is portable and comprises an elongated flexible tube 10, a housing 11 integrally formed with a rear end of the tube 10 and including a space 111, a hand grip 12 extending downward from the housing 11, a working channel 13 extending through both the tube 10 and the housing 11, a tunnel 14 extending from the space 111 to a front end of the tube 10, an electronic visual display (e.g., liquid crystal display (LCD)) 15 disposed on top of the housing 11, and a plurality of buttons 16 disposed on the housing 11 and in front of the display 15.

A processor module 18 is disposed in both the space 111 and the tunnel 14 and comprises a light source (e.g., light-emitting diode (LED)) 181 disposed in the front end of the tunnel 14, a lens 182 disposed adjacent to the light source 181, an electronic image sensor 183 for recording images of a target (e.g., extradural hematoma) 5, the electronic image sensor 183 being implemented as charge-coupled device (CCD) or complementary metal oxide semiconductor (CMOS), an image processing unit 184 disposed in the space 111, a switching member 185 disposed on the housing 11 and electrically connected to an external power source (not shown), and a mass storage unit (i.e., memory) 186 being a semiconductor memory (e.g., flash memory such as CompactFlash card, SmartMedia memory card, MultiMediaCard, Secure Digital (SD) card), dynamic random access memory (DRAM), or static random access memory (SRAM).

In an alternative embodiment, the processor module 18 is powered by an embedded battery so that the endoscope 1 can be made portable.

The buttons 16 are connected to one ends of first, second, third, and fourth wires 171, 172, 173, and 174 respectively. The first, second, third, and fourth wires 171, 172, 173, and 174 are adapted to slide by pressing the buttons 16 and equally spaced through an inner surface of the tube 10. The other ends of the first, second, third, and fourth wires 171, 172, 173, and 174 are secured to the front end of the tube 10.

A surgical instrument guide device 2 comprises a base member 21, an adjustment member 22, a catch 23, a cap member 24, three screws 25, and a tubing 26. The base member 21 is a hollow, shallow cylinder and comprises a center hole 211 through the bottom, a threaded inner surface 212, three through holes 213 through the bottom and equally spaced around the center hole 211, three positioning holes 214 in the bottom and equally spaced around the center hole 211, and three holed legs 215 extending downward from the underside, the holed legs 215 being cylindrical and communicating with the through holes 213.

The elongated, hollow, cylindrical adjustment member 22 comprises a universal joint 221 at one end, a lower portion of the universal joint 221 being pivotably disposed in a half-spherical mouth at the top end of the center hole 211, a cylindrical shank 222, and a channel 223 through the shank 222.

The catch 23 is a hollow, shallow cylinder and comprises a central hole 231 through the bottom, and three pegs 232 on the underside being equally spaced around the central hole 231. The pegs 232 are fitted in the positioning holes 214. The curved surface of the central hole 231 is fastened by an upper portion of the universal joint 221. Thus, the catch 23 is fastened. Also, the universal joint 221 is held in place.

The cap member 24 is shaped as a nut and comprises a longitudinal through hole 241 and a threaded shank 242 secured to the threaded inner surface 212 to fasten the catch 23 in a lower portion of the through hole 241. And in turn, the universal joint 221 is fastened by the catch 23. As such, the adjustment member 22 is anchored. The shank 222 of the adjustment member 22 extends out of the through hole 241. The three screws 25 are disposed through the through holes 213 and legs 215 into the skull 3 to secure the surgical instrument guide device 2 to the skull 3. The tubing 26 comprises an enlarged head 261 and a longitudinal through hole 262. The tubing 26 is disposed in the channel 223 to have its head 261 rested upon the annually flanged top of the shank 222.

Figure 5:
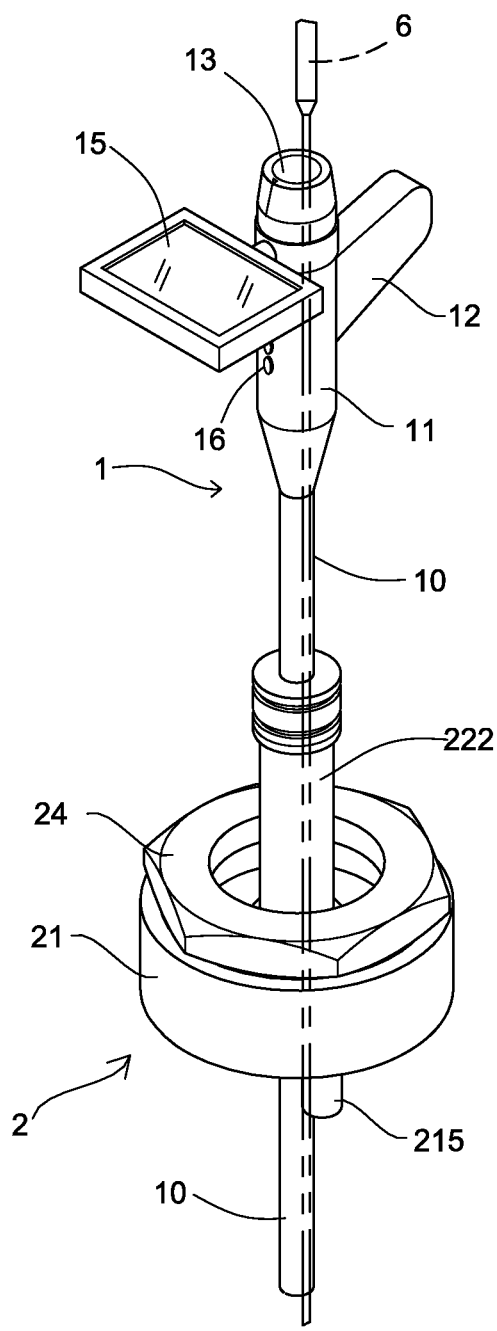
FIG. 5 is a perspective view of the surgical instrument inserted through the endoscope which is in turn inserted through a surgical instrument guide device.
Figure 6:
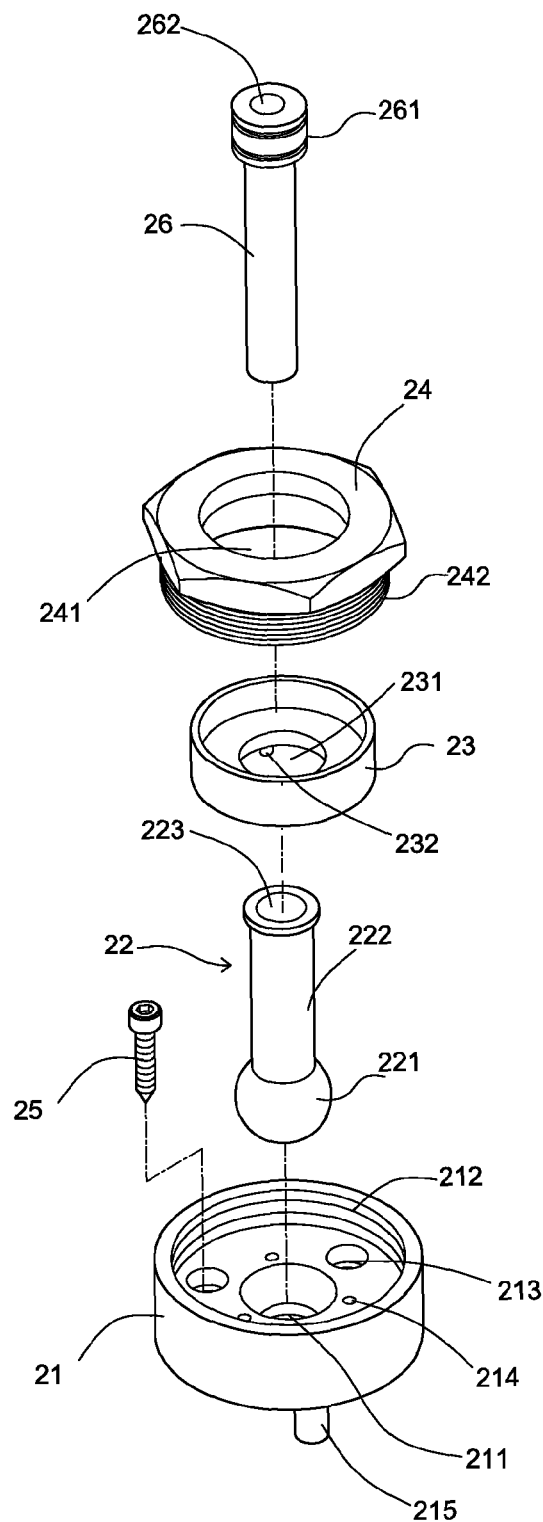
FIG. 6 is an exploded view of the surgical instrument guide device.
Figure 7:
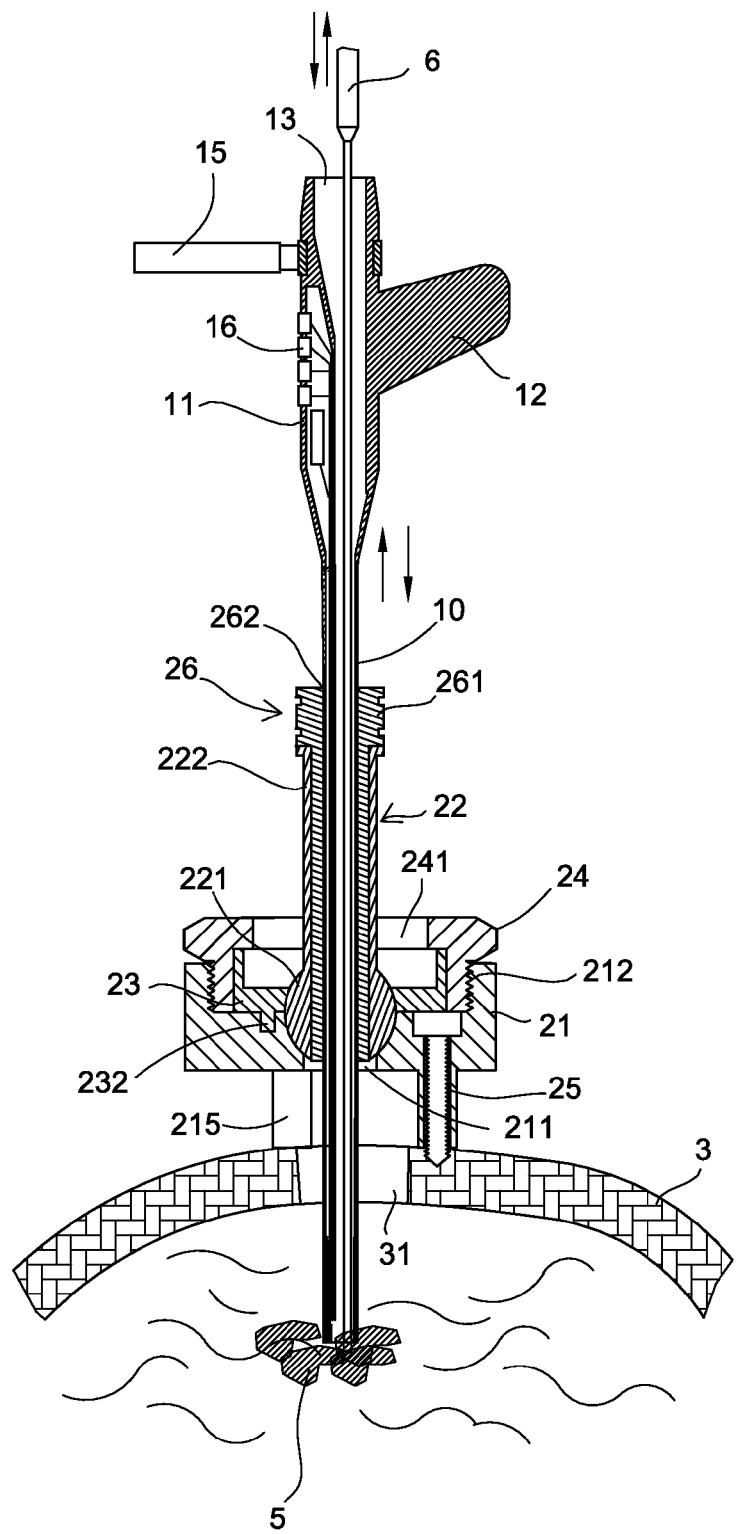
FIG. 7 is a longitudinal sectional view showing the surgical instrument guide device temporarily secured to the skull, the endoscope moveably guided by the surgical instrument guide device and inserted into the cranial cavity, and the surgical instrument inserted through the endoscope to contact an extradural hematoma during an endoscopy.

As shown in FIGS. 5 and 7, an endoscopy is illustrated in a preferred embodiment of the invention. The endoscope 1 is disposed through the surgical instrument guide device 2, the bottom of the surgical instrument guide device 2 is threadedly secured to the skull 3, and the front end of the tube 10 is inserted through a hole 31 of the skull 3 and a cranial cavity to contact an extradural hematoma 5. A medical employee (e.g., physician) may then activate the processor module 18 by pressing the switching member 185 to turn on the light source 181 and other components of the processor module 18. And in turn, light rays emitted by the light source 181 may impinge on the extradural hematoma 5 (i.e., focusing). The physician may press one or more of the first, second, third, and fourth wires 171, 172, 173, and 174 to pivot the front end of the tube 10 (i.e., the light source 181) until the extradural hematoma 5 is focused if the extradural hematoma 5 was not focused. Next, the physician may insert an elongated surgical instrument (e.g., electrical burning knife, sucking tube, or the like) 6 through the working channel 13 of the endoscope 1 to contact the extradural hematoma 5. The lens 182 can take a video image of the extradural hematoma 5. The image sensor 183 can record the images of the extradural hematoma 5 taken by the lens 182. The image processing unit 184 can process the recorded images into digital images to be shown on the display 15. Thus, the physician can manipulate the surgical instrument 6 by closely watching enlarged images of the extradural hematoma 5 shown on the display 15. As a result, the extradural hematoma 5 can be successfully removed out of the brain. It is noted that the digital images of the extradural hematoma 5 can be stored in the mass storage unit 186 for future reference.

In an alternative embodiment of the invention, the surgical instrument guide device 2 can be eliminated from the operation if the target of a patient is throat, oral cavity, or the like. Detailed description of the operation is omitted herein because it is substantially the same as that described in above paragraph.

While the invention has been described in terms of preferred embodiments, those skilled in the art will recognize that the invention can be practiced with modifications within the spirit and scope of the appended claims.

What is claimed is:

1. An apparatus, comprising:

an endoscope comprising an elongated flexible tube; a housing integrally formed with the tube and including a space; a working channel extending through both the tube and the housing; a tunnel extending from the space to the tube; a plurality of buttons disposed on the housing; a processor module disposed in both the space and the tunnel; and an electronic visual display disposed on the housing; and a surgical instrument guide device for temporarily securing the endoscope to an organ of a patient;

wherein an elongated surgical instrument is allowed to insert through the working channel to cooperate with the processor module; and wherein the surgical instrument guide device comprises a base member, an adjustment member, a catch, a cap member, a plurality of fasteners, and a tubing; and wherein the base member is a hollow cylinder and comprises a center hole through bottom, a threaded inner surface, a plurality of through holes through the bottom, a plurality of positioning holes in bottom, and a plurality of holed legs extending downward from underside, the holed legs communicating with the through holes; the adjustment member comprises a universal joint at one end, a lower portion of the universal joint being pivotably disposed in a half-spherical upper mouth of the center hole, a cylindrical shank, and a channel through the shank; the catch is a hollow cylinder and comprises a central hole through bottom and being fastened by an upper portion of the universal joint, and a plurality of bottom pegs; the cap member is cylindrical and comprises a longitudinal hole with the shank of the adjustment member extending through, and a threaded shank secured to the threaded inner surface to fasten the catch in a lower portion of the longitudinal through hole and fasten the universal jointer; the fasteners are disposed through the through holes and legs; and the tubing is hollow and disposed in the channel of the adjustment member to have its enlarged head rested upon the shank of the adjustment member.

2. The apparatus of claim 1, wherein the pegs of the catch are fitted in the positioning holes of the base member.

3. The apparatus of claim 1, wherein the tube of the endoscope is inserted through the tubing of the surgical instrument guide device so as to dispose in close proximity to a target, and the surgical instrument guide device is allowed to insert through the working channel to contact the target.

* * * * *